(12) United States Patent
Hermetter et al.

(10) Patent No.: US 7,772,402 B2
(45) Date of Patent: Aug. 10, 2010

(54) OPTICALLY DETECTABLE ORGANOPHOSPHONATES

(75) Inventors: Albin Hermetter, Graz (AT); Olga Oskolkova, Graz (AT)

(73) Assignee: Austria Wirtschaftsservice Gesellschaft Mit Beschrankter Haftung, Vienna (AT)

( * ) Notice: Subject to any disclaimer, the term of this patent is extended or adjusted under 35 U.S.C. 154(b) by 0 days.

(21) Appl. No.: 12/490,217

(22) Filed: Jun. 23, 2009

(65) Prior Publication Data

US 2009/0258422 A1    Oct. 15, 2009

Related U.S. Application Data

(60) Division of application No. 11/228,987, filed on Sep. 16, 2005, now Pat. No. 7,601,845, which is a continuation of application No. PCT/AT2004/000058, filed on Feb. 26, 2004.

(30) Foreign Application Priority Data

Mar. 19, 2003   (AT) ............................... A 440/2003

(51) Int. Cl.
    *C07F 9/40*  (2006.01)
(52) U.S. Cl. ...................................... 548/112; 558/170
(58) Field of Classification Search ................. 548/112; 558/170
    See application file for complete search history.

(56) References Cited

OTHER PUBLICATIONS

Oskolkova, Olga V. et al., "Fluorescent organophosphonates as inhibitors of microbial lipases", Chemistry and Physics of Lipids, vol. 125, 2003, pp. 103-114.

Silvius, John R. et al., "Novel fluorescent phospholipids for assays of lipid mixing between membranes", Biochemistry, 1987, vol. 26, No. 14, pp. 4279-4287.

Schutz, Gerhard J. et al., "Properties of lipid microdomains in a muscle cell membrane visualized by single molecule microscopy", The EMBO Journal, Mar. 1, 2000, vol. 19, No. 5, pp. 892-901.

Davenport, Lesley et al., "A novel fluorescent coronenyl-phospholipid analogue for investigations of submicrosecond lipid fluctuations", Chemistry and Physics of Lipids, vol. 109, No. 2, Feb. 2001, pp. 145-156.

Rasmussen, Jo-Anne M. et al., "Chemical synthesis of fluorescent glycero- and sphingolipids", Progress in Lipid Research, vol. 47, 2008, pp. 436-460.

*Primary Examiner*—Joseph R Kosack
(74) *Attorney, Agent, or Firm*—Birch, Stewart, Kolasch & Birch, LLP

(57) ABSTRACT

The invention relates to compounds having general formula I (I)

Figure 1:
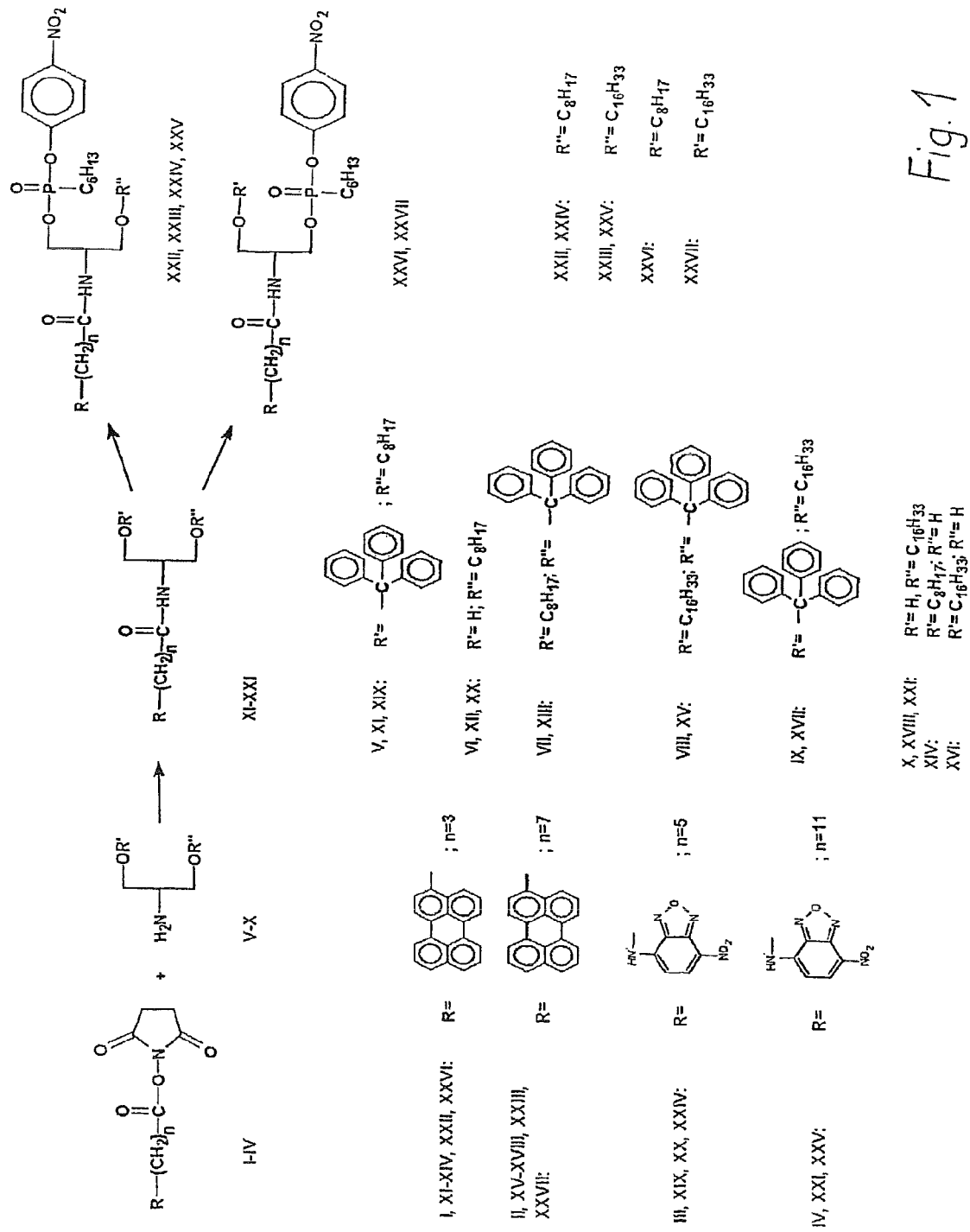

in which X represents an optically detectable moiety, n is an integer with $1 \leq n \leq 20$, $R_1$ is an unbranched or branched alkyl group having 1 to 20 carbon atoms, and $R_2$ is hydrogen or —$CH_2$—O—$R_3$ group, wherein $R_3$ has the same meaning as $R_1$. These compounds are useful as inhibitors of lipolytic enzymes and can be used as tools for analysis as well as discrimination of lipolytic enzymes in biological samples.

8 Claims, 3 Drawing Sheets

OPTICALLY DETECTABLE ORGANOPHOSPHONATES

This application is a Divisional of co-pending application Ser. No. 11/228,987 filed on Sep. 16, 2005, and for which priority is claimed under 35 U.S.C. §120, which is a continuation of International Application No. PCT/AT2004/000058 filed on Feb. 26, 2004; and this application claims priority of Application No. A 440/2003 filed in Austria on Mar. 19, 2003; the entire contents of all are hereby incorporated by reference.

The present invention relates to optically detectable organophosphonates. In particular, it relates to fluorescent organophosphonates which are lipase inhibitors.

Lipolytic enzymes are widely used biocatalysts in research and industry to achieve chemical reactions with high regio-, and stereoselectivity yielding enantiomeric alcohols or amines (Jaerger et al., Trends Biotech. 16, 396-403 (1998); Schmid, R. and Verger, R. D., Angew. Chem. 110, 1694-1720 (1998); Schmid et al., Nature 409, 258-268 (2001); Koeller et al., Nature 409, 232-240 (2001); Klibanov, Nature 409, 241-246 (2001)).

Lipases catalyze hydrolysis and synthesis of triacylglycerols. All lipases accept esters of medium (C4) and long-chain (C16) saturated fatty acids as substrates, mainly at sn-1 or sn-3 positions (Rangheard et al., Enzyme Microb. Technol. 14, 966-974 (1992); Kirk et al., Biocatalysis 6, 127-134 (1992); Ransac et al., J. Biol. Chem. 265, 20263-20270 (1990); Rogalska et al., Chirality 5, 24-30 (1993)).

The mechanism of action of these enzymes involves the nucleophilic cleavage of an ester bond by an activated serine which belongs to the catalytic triad Ser-His-Asp/Glu (Cygler et al., Methods Enzymol. 284, 3-27 (1997); Jaeger et al., see above; Schmid, R. and Verger, R. D., see above).

Lipophilic p-nitrophenyl phosphonate esters are convenient tools in lipase research, e.g., for studies of substrate-enzyme interactions on the molecular level (Ransac et al., Methods Enzymol 186, 190-231 (1997)) and functional analysis, e.g., to determine the active enzyme fraction of crude or pure protein preparations (Scholze et al., Analyt. Biochem. 276, 72-80 (1999); Rotticci et al., Biochim. Biophys. Acta 1483, 132-140 (2000)).

These inhibitors react with the nucleophilic serine of lipases, thus leading to the formation of covalent and equimolar lipid-protein complexes that are stable in aqueous and organic solutions (Rotticci et al., see above; Ransac et al., 1997, see above; Bjoerkling et al., Biorgan. Med. Chem. 2, 697-705 (1994); Zandonella et al., Eur. J. Biochem. 262, 63-69 (1999)). Such complexes represent "open" lipase conformations and mimic the substrate-enzyme interactions in the first (tetrahedral) transition state.

Fluorescent labels in the hydrophobic tail of the organophosphonates are not only useful for quantitative analysis of lipases but also for studying lipid-protein interactions in the first transition state under different environment (solvent) conditions (Oskolkova, O. V. and Hermetter, A., Biochim. Biophys. Acta 1597, 60-66 (2002); Zandonella et al., see above).

However, there is a need for further compounds for analytical and mechanistic studies on lipolytic enzymes.

Accordingly, it is the object of the present invention to provide compounds which are useful as inhibitors of lipolytic enzymes. In particular, these compounds should be useful tools for analysis as well as discrimination of lipolytic enzymes in biological samples.

This object is achieved by compounds having general formula I

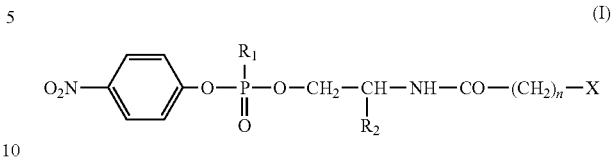

in which X represents an optically detectable moiety, n is an integer with $1 \leq n \leq 20$, $R_1$ is an unbranched or branched alkyl group having 1 to 20 carbon atoms, and $R_2$ is hydrogen or —$CH_2$—O—$R_3$ group, wherein $R_3$ has the same meaning as $R_1$.

Preferably, n is an integer with $3 \leq n \leq 11$.

In a preferred embodiment, $R_1$ is hexyl and $R_2$ is —$CH_2$—O—$R_3$ group with $R_3$ being octyl or hexadecyl.

According to a further preferred embodiment, $R_1$ is methyl and $R_2$ is —$CH_2$—O—$R_3$ group with $R_3$ being octyl or hexadecyl.

According to another preferred embodiment, $R_1$ is butyl and $R_2$ is —$CH_2$—O—$R_3$ group with $R_3$ being octyl or hexadecyl.

In another preferred embodiment, the optically detectable moiety is a fluorophore, preferably a perylene, pyrene or nitrobenzoxadiazole (NBD) group.

According to a further aspect, the present invention relates to the use of the new compounds for inhibiting lipolytic enzymes. It further relates to the use of the new compounds for the determination and/or discrimination of lipolytic enzymes in biological samples.

Di-O-alkylglycero-phosphonates have already been reported as useful inhibitors of lipase activity (Stadler et al., Biochim. Biophys. Acta 1304, 229-244 (1996); Zandonella et al., see above). However, there was no suggestion that microbial lipases would react with fluorescent phosphonate inhibitors containing amide bonds.

It has been found that the compounds according to the present invention are able to inhibit microbial lipases. Moreover, the compounds according to the present invention have been found to have different inhibitory effects on the activity of different lipases, thereby allowing discrimination of lipolytic enzymes.

Figure 2:
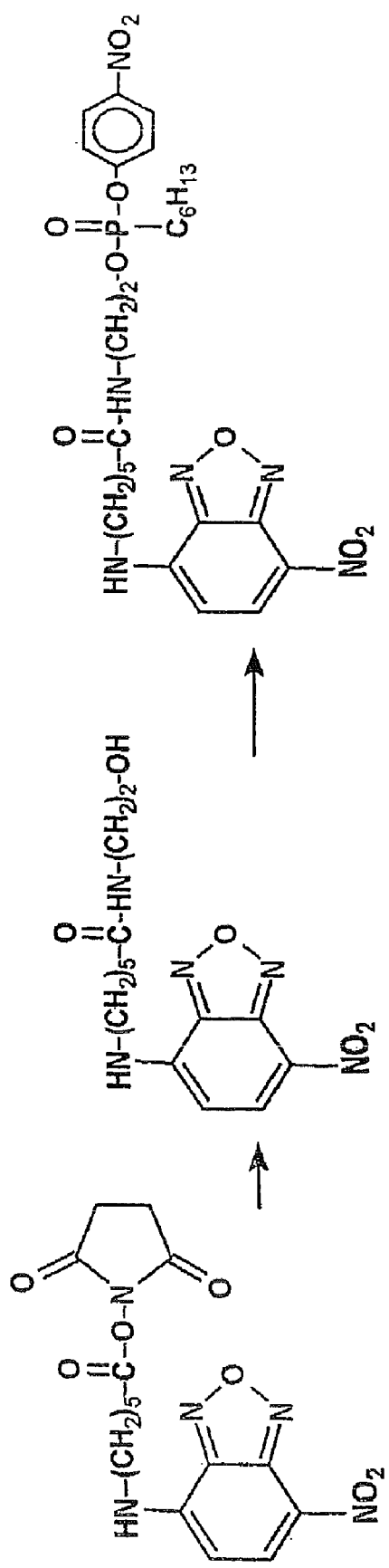
Figure 3A:
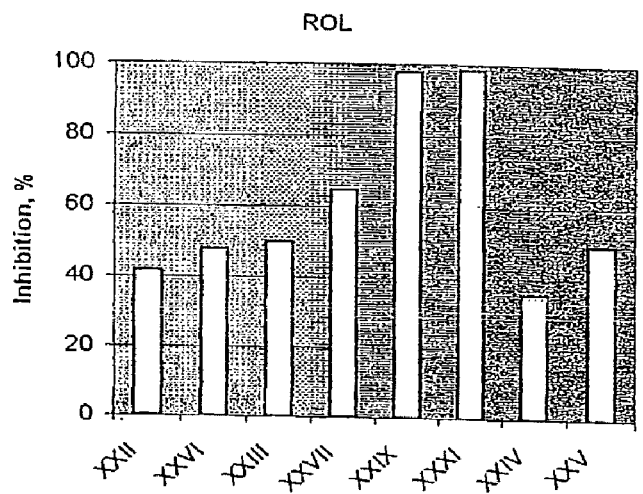
Figure 3B:
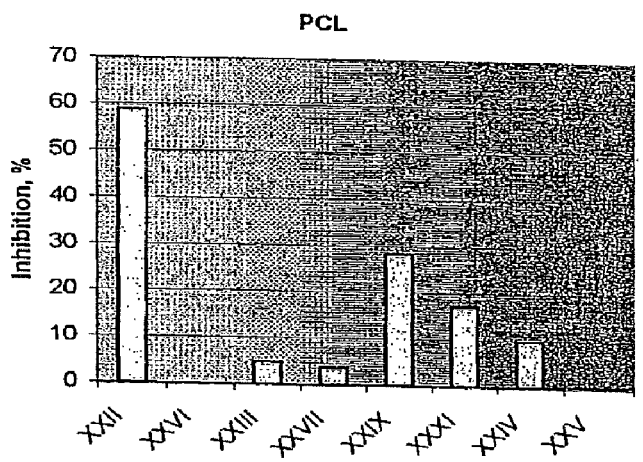
Figure 3C:
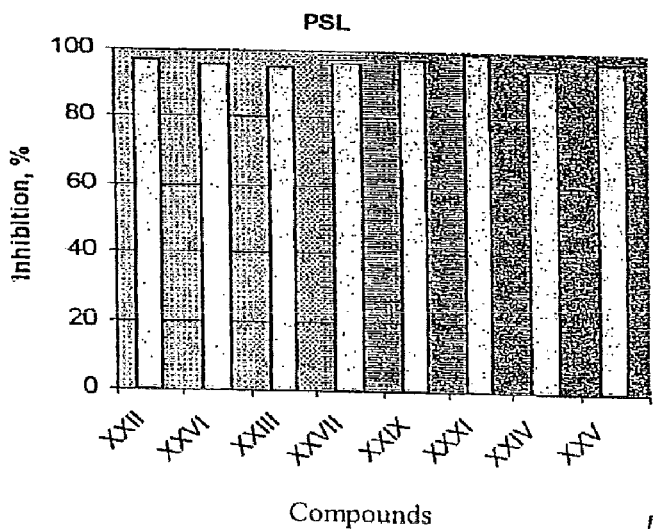

The invention will now be described in more detail by way of the following examples and figures, wherein FIG. 1 illustrates synthetic routes of fluorescently labelled organophosphonates according to the present invention;

FIG. 2 illustrates the synthesis of one-chain perylene- and NBD (nitrobenzoxadiazole)-inhibitors according to the present invention; and FIG. 3a to 3c show inhibition of microbial lipases from *Rhizopus oryzae* (ROL), *Pseudomonas cepacia* (PCL) and *Pseudomonas* species (PSL), respectively, in block diagram.

EXAMPLES

Materials and Methods:

Standard chemicals were obtained from Merck. Mercaptoethanol and p-nitrophenol were from Sigma; methyl phosphonic acid dichloride, n-hexylphosphonic acid dichloride and methyl sebacoyl chloride were from Aldrich. 1-Methylimidazole, tetrazole (3.5% solution in acetonitrile, from Sigma-Aldrich), perylene, 3-carbomethoxypropionyl chloride, and N-hydroxysuccinimide were obtained from Fluka.

Succinimidyl 6-[N-(7-nitrobenz-2-oxa-1,3-diazol-4-yl)amino]hexanoate was purchased from Molecular Probes, 12-[N-(7-nitrobenz-2-oxa-1,3-diazol-4-yl)amino]dodecanoic acid from Lambda Fluoreszenztechnologie GmbH (Graz, Austria).

Activated succinimide esters of fluorescently labelled acids were synthesized from appropriate fatty acids and N-hydroxysuccinimide in the presence of dicyclohexylcarbodiimide by a procedure essentially described elsewhere (Lapidot et al., J. Lipid Res. 8, 142-145 (1967)).

The synthesis of 2-amino-2-deoxy-1(3)-O-trityl-3(1)-O-alkyl-sn-glycerols was performed in our laboratory according to Bucher, Ribitsch et al. (unpublished) (however, also see Doris Ribitsch, PhD-Thesis, Technical University of Graz, 2002).

Crude *Pseudomonas* species lipase was purchased from Nagase Biochemicals Ltd. (Japan), the pure lipase from *Pseudomonas cepacia* (PCL) was obtained from R.D. Schmid, University of Stuttgart, Germany. *Rhizopus oryzae* lipase was kindly provided by F. Spener and L. Haalck, University of Münster, Germany.

Dichloromethane (Riedel-de Haën) was dried by refluxing with phosphorus pentoxide (Merck) and subsequently distilled. Other solvents were of analytical grade.

TLC was carried out on silica gel 60 $F_{254}$ aluminum sheets (0.2 mm, Merck) using following mixtures: petroleum ether/ether, 2:1, v/v (system 1), chloroform/methanol/acetone, 10:0.2:0.2, v/v/v (system 2), or chloroform/methanol/acetone, 10:0.5:0.5, v/v/v (system 3) as developing solvents. For preparative TLC purification silica gel 60 aluminum sheets (0.2 mm, Merck) without fluorescent indicator were used.

Compounds were visualized under UV-light (360 nm) and by charring at 120° C. after spraying with 50% sulfuric acid. Phosphorus-containing compounds were visualized on TLC plates by staining with phosphomolybdic acid (Dittmer & Lester, J. Lipid Res. 5, 126-127 (1964)), or quantitatively determined in solutions by the method of Broekhuyse (Biochim. Biophys. Acta 260, 449-459 (1968)).

Short column chromatography was performed on Kieselgel (silica gel) 60 (230-400 mesh, Merck). $^1$H-NMR spectra were recorded in deuterated solvents at 199.97 MHz, using a Varian Gemini 200 spectrometer. Chemical shifts ($\delta$) are given in ppm relative to tetramethylsilane as a standard.

Positive ion ESI mass spectra were recorded on a standard Kratos electrospray ion source that was fitted to a Kratos Profile HV-4 double-focusing magnetic sector instrument (acceleration voltage 2 kV, m/z-range 25 to 2400 Da, scan speed 10 s/Dec, resolution 1700 (10% valley)). The potentials applied to the ESI source (temperature 50° C., countercurrent flow of nitrogen 150 mL/min) were +5.98 kV at the spraying capillary, +3.12 kV at the cylinder, and +2.57 kV at the endplate. A Harvard Apparatus 22 syringe pump was used to deliver a constant flow (6 μL/min) of dry methanol containing CsI (250 mg/L). Solutions of the samples (50 μM) in the same solvent were injected via a 100-μL sample loop. The m/z values are given for the most intense peak of any isotope distribution.

3-(3-Perylenoyl)propanoic acid methyl ester

To a solution of 3-carbomethoxypropionyl chloride (51.8 μL, 0.415 mmol) in 10 mL dichloromethane, 64.7 mg (0.476 mmol) aluminum chloride were added in portions under stirring at 0° C. The reaction was kept at this temperature for 1 h and then 100.0 mg (0.396 mmol) perylene were added portionwise. The mixture was kept at 0° C. for 1 h and then overnight at room temperature, poured on about 10 g of ice, acidified with 1-3 drops concentrated hydrochloric acid. The product was extracted with dichloromethane (6×50 mL), washed with water (2×10 mL). The organic layers were dried over sodium sulfate. After evaporation, the residue was purified by column chromatography on silica gel eluting with chloroform to give the pure product perylenoylpropanoic acid methyl ester (121.2 mg, 83.5%). $R_f$ 0.16 (system 1). $^1$H-NMR (CDCl$_3$) ($\delta$, ppm): 2.87 (t, 2H, $J_{a,b}=J_{2,3}$ 6.52 Hz, 2-CH$_2$—COO—), 3.40 (t, 2H, $J_{a,b}=J_{2,3}$ 6.51 Hz, 3-CH$_2$—CO—Ar), 3.77 (s, 3H, CH$_3$—OCO—), 7.47-7.65 (m, 3H, Ar), 7.74 (t, 2H, J 8.63 Hz, Ar), 7.95 (d, 1H, J 8.01 Hz, Ar), 8.14-8.31 (m, 3H, Ar), 8.56 (d, 1H, J 8.57 Hz, Ar).

4-(3-Perylenyl)butanoic acid

To a suspension of 3-perylenoyl propanoic acid methyl ester (360.2 mg, 0.983 mmol) in 2.0 mL diethylene glycol, 98% hydrazine hydrate (150.6 μL, 2.949 mmol) and powdered potassium hydroxide (275.3 mg, 4.916 mmol) were added. The reaction mixture was heated to 140° C. for 2 hrs, then to 190° C. and kept over night, cooled to room temperature, diluted with 20 mL water, acidified with 0.5 mL concentrated hydrochloric acid, the precipitate formed was filtered, washed with water to pH 7.0, dried on air or washed with acetone, then with a mixture chloroform-methanol (8:2 by vol.). The filtrate was concentrated in vacuo. The crude product was applied onto a silica gel column and eluted with chloroform to 20% methanol in chloroform to give perylenebutanoic acid (228.9 mg, 68.8%). $R_f$ 0.66 (system 3). $^1$H-NMR (CDCl$_3$/DMSO-d$_6$, 20:1) ($\delta$, ppm): 1.92 (quin., 2H, 3-CH$_2$), 2.38 (t, 2H, J 7.00 Hz, 2-CH$_2$), 3.03 (t, 2H, J 7.00 Hz, 4-CH$_2$), 7.41 (d, 1H, J 7.82 Hz, Ar), 7.43-7.64 (m, 3H, Ar), 7.76 (d, 1H, J 3.42 Hz, Ar), 7.80 (d, 1H, J 3.41 Hz, Ar), 8.00 (d, 1H, J 8.49 Hz, Ar), 8.21-8.60 (m, 4H, Ar).

7-(3-Perylenoyl)heptanoic acid methyl ester

The synthesis and purification of perylenoylheptanoic acid methyl ester was achieved as described for perylenoyl propanoic acid methyl ester starting from sebacic acid monomethyl ester chloride and perylene. Yield 73.7%. $R_f$ 0.23 (system 1). $^1$H-NMR (CDCl$_3$) ($\delta$, ppm): 1.43 (m, 4H, 4-CH$_2$, 5-CH$_2$), 1.67 (m, 2H, 3-CH$_2$), 1.82 (m, 2H, 6-CH$_2$), 2.32 (t, 2H, $J_{a,b}=J_{2,3}$ 7.42 Hz, 2-CH$_2$), 3.05 (t, 2H, $J_{a,b}=J_{6,7}$ 7.35 Hz, 7-CH$_2$), 3.69 (s, 3H, CH$_3$), 7.43-7.64 (m, 3H, Ar), 7.74 (t, 2H, J 8.26 Hz, Ar), 7.84 (d, 1H, J 7.92 Hz, Ar), 8.13-8.30 (m, 4H, Ar), 8.48 (d, 1H, J 7.54 Hz, Ar).

8-(3-Perylenyl)octanoic acid

The synthesis and isolation was accomplished under identical conditions as described for perylenebutanoic acid starting from 7-(3-perylenoyl)heptanoic acid methyl ester yielding 60.0% perylenyloctanoic acid. $R_f$ 0.63 (system 3). $^1$H-NMR (CDCl$_3$/CD$_3$OD, 9:1) ($\delta$, ppm): 1.25-1.50 (m, 6H, 3(CH$_2$)), 1.59 (m, 2H, 3-CH$_2$), 1.72 (m, 2H, 7-CH$_2$), 2.26 (dt, 2H, $J_{a,b}$ 1.79 Hz, $J_{2,3}$ 7.45 Hz, 2-CH$_2$), 2.97 (t, 2H, $J_{7,8}$ 7.72 Hz, 8-CH$_2$), 7.28 (d, 1H, J 8.0 Hz, Ar), 7.43 (m, 3H, Ar), 7.59 (d, 1H, J 3.42 Hz, Ar), 7.63 (d, 1H, J 3.42 Hz, Ar), 7.83 (d, 1H, J 8.54 Hz, Ar), 8.10-8.22 (m, 4H, Ar).

2-(4-(3-Perylenyl)butanoyl)amino-2-deoxy-3-O-octyl-sn-glycerol (XII)

A) To a solution of 12.0 mg (0.027 mmol) perylenebutyric acid succinimide ester (I) in 3 mL THF, 2-amino-2-deoxy-1-

O-trityl-3-O-octyl-sn-glycerol (V) (12.2 mg, 0.027 mmol) was added. The reaction mixture was kept at room temperature overnight, evaporated under a stream of argon. The residue was applied onto a silica gel column and eluted with chloroform. Fractions containing the product were collected and the solvent was removed under reduced pressure. The compound (XI) (20.8 mg) was obtained with 98.6% yield. $R_f$ 0.81 (system 2). Removal of the trityl blocking group from 2-perylenebutanoylamino-1-O-trityl-3-O-octyl-sn-glycerol (XI) was carried out with boron trifluoride-methanol in absolute dichloromethane under procedure elaborated by Hermetter et al. (Chem. Phys. Lipids 50, 57-62 (1989)). Yield 70.0%.

B) The compound (XII) was achieved by an analogous procedure described above starting from perylenebutanoic acid succinimide ester (I) and 2-amino-2-deoxy-3-O-octyl-sn-glycerol (VI) with 91.0% yield. The products obtained in both cases were identical.

2-(4-(3-Perylenyl)butanoyl)amino-2-deoxy-1-O-octyl-sn-glycerol (XIV)

The compound (XIV) was obtained from an equimolar mixture of perylenebutanoic acid succinimide ester (I) and 2-amino-2-deoxy-1-O-octyl-3-O-trityl-sn-glycerol (VII) under identical conditions described in method (A) for (XII). Overall yield after two stages was 88.3%.

2-(8-(3-Perylenyl)octanoyl)amino-2-deoxy-1-O-hexadecyl-sn-glycerol (XVI)

This product was synthesized using the same procedure as for (XII) (procedure A) starting from peryleneoctanoic acid succinimide ester (II) and 2-amino-2-deoxy-1-O-hexadecyl-3-trityl-sn-glycerol (VIII). Yield (after two stages) 90.0%.

2-(8-(3-Perylenyl)octanoyl)amino-2-deoxy-3-O-hexadecyl-sn-glycerol (XVIII)

The compound (XVIII) was prepared in 67.9% yield by the same procedure as described for (XII) (A), starting from amino glycerol (IX) and peryleneoctanoic acid succinimidyl ester 2-(6-NBD-hexanoyl)amino-2-deoxy-3-O-octyl-sn-glycerol (XX)

The amino glycerol (XX) was obtained from NBD-hexanoic acid succinimide ester (III) and 2-amino-2-deoxy-1-O-trityl-3-octyl-sn-glycerol (V) as described for (XII) (A). Yield 86.0%. Alternatively, the same compound (XX) was prepared under identical conditions as for (XII) method (B) but using succinimide ester (III) and 2-amino-2-deoxy-3-O-octyl-sn-glycerol (VI) with a 100% yield.

2-(6-NBD-dodecanoyl)amino-2-deoxy-3-O-hexadecyl-sn-glycerol (XXI)

The synthesis of the long-chain alkyl acylamino glycerol (XXI) was achieved under identical conditions as described for the compound (XII) (method B) starting from NBD-dodecanoic acid succinimide ester (IV) and 2-amino-2-deoxy-3-O-hexadecyl-sn-glycerol (X). The yield comprised 98.0%.

2-(4-(3-Perylenyl)butanoyl)amino-2-deoxy-3-O-octyl-sn-glycero-1-O-hexylphosphonate p-nitrophenyl ester (XXII)

To a solution of the glycerol derivative (XII) (20.0 mg, 0.038 mmol), 40 µL triethylamine, and 3.5% tetrazole solution in acetonitrile (7.4 µL, 0.004 mmol) in 2 mL dichloromethane, hexyl phosphonic acid dichloride (12.9 µL, 0.076 mmol) was added at 5° C. After 1 h when the reaction was complete, p-nitrophenol (10.6 mg, 0.076 mmol) was added and the reaction mixture was kept overnight at room temperature. The solvent was removed under a stream of nitrogen. The product was isolated by preparative TLC in the enveloping system chloroform/methanol/acetone, 10:0.2:0.2 by vol. Yield 13.1 mg (43.3%). $^1$H-NMR (CDCl$_3$) (δ, ppm): 0.87 (t, 6H, 2CH$_3$), 1.05-2.00 (m, 22H, CH$_2$-alkyl), 2.13 (m, 2H, 2-CH$_2$-acyl), 2.30 (m, 2H, 3-CH$_2$-acyl), 3.05 (m, 2H, CH$_2$—O-alkyl), 3.40 (m, 4H, CH$_2$-O-glycerol, 4-CH$_2$-acyl), 4.25 (m, 3H, CH$_2$—O—P, CH—N), 6.18 (dd, 1H, NH), 7-29-7.40 (m, 3H, Ar), 7.50 (m, 3H, Ar), 7.66 (d, 1H, J 39 Hz, Ar), 7.70 (d, 1H, J 2.19 Hz, Ar), 7.89 (dd, 1H, J 3.42 Hz, J 8.06 Hz, Ar), 8.17 (m, 6H, Ar).

2-(4-(3-Perylenyl)butanoyl)amino-2-deoxy-1-0-octyl-sn-glycero-3-O-hexylphosphonate p-nitrophenyl ester (XXVI)

To a solution of 2-perylenebutanoylamino-1-O-octyl-sn-glycerol (XIV) (8.1 mg, 0.016 mmol) and N-methylimidazole (6.0 µL, 0.070 mmol) in 2 mL dichloromethane, n-hexylphosphonic dichloride (10.8 µL, 0.063 mmol) was added. The reaction mixture was kept at room temperature for 3 hrs. After the reaction was complete, a mixture of p-nitrophenol (10.6 mg, 0.076 mmol) and N-methylimidazole (6.0 µL, 0.070 mmol) were added. After 18 hrs, the solvent was evaporated under a stream of argon. The phosphonate (XXVI) was purified by TLC in system 2. Yield 0.7 mg (5.7%).

2-(8-(3-Perylenyl)octanoyl)amino-2-deoxy-3-O-hexadecyl-sn-glycero-1-O-hexylphosphonate p-nitrophenyl ester (XXIII)

The phosphonate (XXIII) was prepared under identical conditions as described for (XXII) with 6.3% yield and under conditions as for (XXIV) as well (yield 31.6%) starting from (XVIII).

2-(8-(3-Perylenyl)octanoyl)amino-2-deoxy-1-O-hexadecyl-sn-glycero-3-O-hexylphosphonate p-nitrophenyl ester (XXVII)

The synthesis and isolation was accomplished according to the procedure described for (XXII) starting from the amino glycerol analogue (XVI). Yield 26.1%.

2-(NBD-hexanoyl)amino-2-deoxy-3-O-octyl-sn-glycero-1-O-hexylphosphonate p-nitrophenyl ester (XXIV)

The product (XXIV) was obtained from fluorescent labeled glycerol (XX) under identical conditions as described for (XXII) with 27.8% yield.

2-(NBD-dodecanoyl)amino-2-deoxy-3-O-hexadecyl-sn-glycero-1-O-hexylphosphonate p-nitrophenyl ester (XXV)

The compound (XXI) was phosphorylated as described for the preparation of phosphonate (XXII) using acylamino 0-alkyl glycerol (XXI) as a starting material. The yield comprised 4.4%.

((6-(7-nitrobenz-2-oxa-1,3-diazol-4-yl)amino)hexanoyl)aminoethanol (XXX)

A mixture of NBD-hexanoic acid succinimidyl ester (12.5 mg, 0.032 mmol) and 2-aminoethanol (2 µL, approx. 0.032 mmol) in 2 mL THF was kept for 30 min. After TLC showed the reaction complete, the solvent was removed under a stream of argon. The residue was dissolved in a chloroform/methanol/water mixture (65:25:4 by vol.) (5 mL), and 1 g of a resin Dowex 50W×8 (H$^+$-form) was added. After stirring for 30 min, the product (XXX) dissolved was filtered and the resin was washed with the same solvent system (3×5 mL). The filtrate was evaporated under reduced pressure. TLC analysis showed single fluorescent spot with $R_f$ 0.69 and no aminoethanol after spraying with ninhydrine. Yield 10.6 mg (98.3%).

O-(((6-(7-nitrobenz-2-oxa-1,3-diazol-4-yl)amino) hexanoyl)aminoethyl-O-(p-nitrophenyl) n-hexylphosphonate (XXXI)

Using the method described for phosphonate (XXII), NBD-labeled hexylphosphonate was obtained starting from the respective alcohol (XXX). The yield comprised 11.1%.

Determination of Lipase Activity

Inhibition of lipase activity by the water-insoluble phosphonates was performed in Triton X-100 micelles (2 mM final concentration) and measured by a continuous fluorescence method according to Duque et al, (J. Lipid Res. 37, 868-876 (1996)) using 3-O-hexadecyl-2-pyrenedecanoyl-1-trinitrophenylaminododecanoyl-sn-glycerol as a substrate. Lipase activity was determined at 30° C. from the dequenching of pyrene fluorescence at 378 nm (excitation at 342 nm, slit widths 5.0 nm each) (the initial linear increase in fluorescence intensity after addition of the lipase was used to measure enzyme activity). The measurements were performed in ethanol-water (1:3 by vol.) as a solvent.

Inhibition Experiments

Triton X-100 specially purified for membrane research (Hofmann La Roche) (10 µL of a 100 mM stock solution in chloroform) and the appropriate volume of a phosphonate solution in chloroform were mixed and the solvent was removed under a stream of nitrogen. The residue was dispersed in an 100 µM Tris-HCl puffer (pH 7.40 at 37° C.) by vigorous vortexing followed by addition of an aliquot of a lipase solution, giving a total volume of 500 µL. Incubations were performed at 4° C. The percentage of inhibition after 16 hrs in the reaction mixture was determined by measuring the residual lipase activity of appropriate aliquots (3 µL) as indicated above. Controls were run in parallel under identical conditions but in the absence of inhibitors.

Spectroscopic Analyses

A molar absorbance coefficient of 22000 M$^{-1}$ cm$^{-1}$ at 466 nm in methanol or 29000 M$^{-1}$ cm$^{-1}$ at 442 nm in ethanol for phosphonate inhibitors labelled with NBD or perylene, respectively, was used to determine the concentration of the fluorescent phosphonates (measurements were performed on a Hitachi U-3210 spectrophotometer) (Haugland, Handbook of fluorescent probes, Molecular Probes, p. 293 (1996)).

Results:

Chemical Syntheses

Eight novel phosphonic acid esters fluorescently labeled with perylene butanoic, perylene octanoic, NBD-hexanoic or NBD-dodecanoic acid were synthesized. Perylene and NBD-labels were chosen because of the longer wavelength absorption and emission as compared to pyrene-containing inhibitors, which have been synthesized and characterized previously (Zandonella et al., see above).

For the preparation of perylene labelled lipase inhibitors, the corresponding fluorescently labelled perylene fatty acids were needed. Friedel-Crafts acylation of perylene with appropriate dicarbonic acid monomethyl ester chlorides gave perylenoyl propionic acid methyl ester and perylenoyl heptanoic acid methyl ester. It is known that perylene is only acylated at C-3 position under these reaction conditions (Zinke et al., Ber. B75, 1042-1048 (1940)). The $^1$H-NMR spectra of the synthesized perylenoyl propionic and perylenoyl heptanoic acids (protons of the alkyl and aromatic moieties) confirmed the indicated structures of the acylation products. Kizhner-Wolf reduction of the keto-groups and the concomitant deblocking of the methyl protective groups gave perylenebutanoic and peryleneoctanoic acids, respectively. Proton NMR spectra were in agreement with the ascribed structures.

The synthetic routes leading to the fluorescently labelled triacylglycerol analogues are outlined in FIG. 1. The respective compounds are alkylacyl(amino)deoxyglycerophosphonic acids and alkyloxyphosphonic acid derivatives and three major crucial steps are involved in their synthesis that are: 1) attachment of a fluorescent acyl chain to 1(3)-alkyl-2-aminodeoxy-3(1)-trityl-sn-glycerol, 2) detritylation, and 3) phosphorylation of the resultant alkylacyl(amino)deoxyglycerois.

In principle, the acylation of an amino group can be performed using acid anhydride (Singh et al., J. Carbohydr. Chem. 8, 199-216 (1989)), acyl-halides (Zimmerman et al., j. Carbohydr. Chem. 7, 435-452 (1988); Dijkman et al., Biochim. Biophys. Acta 1043, 67-74 (1990)), mixed carbodiimide (Hammarstroem, J. Lipid Res. 12, 760-765 (1971)), or mixed anhydrides formed by ethylchloroformate and a fatty acid (Acquotti et al., Chem. Phys. Lipids 40, 71-86 (1986)).

These procedures have several disadvantages especially because they require a large molar excess of acylating reagents and long reaction times. The use of acyl chlorides was not convenient in our case because of the possible modification of fatty acid derivatives during acylation. Activated fatty acid esters (for example, p-nitrophenyl esters) have also successfully been applied e.g. for sphingolipid synthesis (Tkaczuk et al., J. Org. Chem. 46, 4393-4398 (1981); Groenberg et al., Biochemistry 30, 10746-10754 (1991); Kann et al., Biochemistry 30, 7759-7766 (1991); Shibuya et al., Chem. Pharm. Bull. 40, 1154-1165 (1992)).

However, acylation with p-nitrophenyl esters of perylene butyric and perylene octanoic acids may give only low yields of acylation products probably because of the close vicinity of a bulky fluorophore and the ester group (Oskolkova et al., Chem. Phys. Lipids 99, 73-86 (1999)). Thus, we used N-hydroxysuccinimide esters of fluorescently labelled fatty acids to acylate selectively amino groups in the presence of free hydroxy groups with high yields (Julina et al., Helv. Chim. Acta 69, 368-373 (1986)). In the present invention, this simple method gave high yields of acylation products (e.g., 91.0% yield of (XII) when 2-amino-2-deoxy-3-O-octyl-sn-glycerol (VI) was acylated with perylenebutanoic acid succinimide ester).

The protective trityl group of the labelled alkylacylaminodeoxytritylglycerols was removed under standard conditions as described for the synthesis of diradylglycerols (Hermetter et al.,/989, see above) using boron trifluoride-methanol. The obtained fluorescent alkylacylaminodeoxyglycerols (XI-XVIII) showed fluorescence spectra typical for perylene-labelled compounds (Johanson et al., J. Am. Chem. Soc. 109, 7374-7381 (1987)).

Two further problems are encountered in the synthesis of fluorescent phosphonate inhibitors. Reaction yields of phosphorylation of glycerolipids tend to be low. Secondly, the fluorescently labelled fatty acids and, as a consequence, the fluorescently labelled glycerolipid intermediates are expensive and this is one special reason why yields should be as high as possible.

The diradylglycerols were reacted with alkylphosphonic acid dichloride in the presence of N-methylimidazole as a base followed by substitution of the second chloro atom at phosphorus by p-nitrophenol. Although these two steps were carried out consecutively in a one-pot reaction, product yields were rather low (5.7% for 2-deoxy-2-(4-perylenylbutanoyl) amino-1-O-octyl-3-O-hexylphosphonate (XXVI) or 6.3% for 2-deoxy-2-(8-perylenyloctanoyl)amino-3-O-hexadecyl-1-O-hexylphosphonate (XXIII)) most likely because of the close vicinity of the amido group to the phosphoric acid moiety, which as a consequence, can lead to an intramolecular cyclic side-product (oxazaphospholane) in considerable amounts.

Such compounds can in fact be prepared from 2-deoxy-2-amino-phosphocholine in the presence of phosphoroxytrichloride (Deigner et al., Chem. Phys. Lipids 61, 199-208 (1992)). To avoid formation of such compounds we used a modification of the phosphorylation procedure as described by Zhao et al. (Tetrahedron Lett. 49, 363-368 (1993)) for the synthesis of phosphonate esters. This approach used tetrazole as a catalyst and has already been shown to be successful for the synthesis of phosphonates from sterically hindered alcohols such as menthol and testosterone (Zhao et al., see above) or for the synthesis of organophosphonate esters (Rotticci et al., see above).

In our case, the yields of products were significantly improved when tetrazole was used as a catalyst (e.g., yields of 2-deoxy-2-(8-peryleneoctanoyl)amino-3-O-hexadecyl-1-O-hexylphosphonate (XXIII) were 6.3% in the absence of tetrazole and 31.6% in its presence (Table 1)). For the other glycerolipid phosphonate analogues, yields were above 25% if synthesized by the tetrazole-catalyzed reaction.

TABLE 1

Comparison of chromatographic characteristics of fluorescent phosphonates synthesized and their yields after phosphorylation.

| Compounds | Number | Chromatographic behavior $R_f$ | Yield of phosphorylation, % without catalyst | Yield of phosphorylation, % with tetrazole as catalyst |
|---|---|---|---|---|
| (perylenyl)-(CH$_2$)$_3$-C(O)-HN-CH(CH$_2$-O-P(O)(C$_6$H$_{13}$)-O-C$_6$H$_4$-NO$_2$)(CH$_2$-O-C$_8$H$_{17}$) | XXII | 0.33$^a$ | n.d. | 43.3 |
| (perylenyl)-(CH$_2$)$_3$-C(O)-HN-CH(CH$_2$-O-C$_8$H$_{17}$)(CH$_2$-O-P(O)(C$_6$H$_{13}$)-O-C$_6$H$_4$-NO$_2$) | XXVI | 0.33$^a$ | 5.7 | n.d. |
| (perylenyl)-(CH$_2$)$_7$-C(O)-HN-CH(CH$_2$-O-P(O)(C$_6$H$_{13}$)-O-C$_6$H$_4$-NO$_2$)(CH$_2$-O-C$_{16}$H$_{33}$) | XXIII | 0.46$^a$ | 6.3 | 31.6 |
| (perylenyl)-(CH$_2$)$_7$-C(O)-HN-CH(CH$_2$-O-C$_{16}$H$_{33}$)(CH$_2$-O-P(O)(C$_6$H$_{13}$)-O-C$_6$H$_4$-NO$_2$) | XXVII | 0.46$^a$ | n.d. | 26.1 |

TABLE 1-continued

Comparison of chromatographic characteristics of fluorescent phosphonates synthesized and their yields after phosphorylation.

| Compounds | Number | Chromatographic behavior $R_f$ | Yield of phosphorylation, % | |
|---|---|---|---|---|
| | | | without catalyst | with tetrazole as catalyst |
| HN—(CH₂)₅—C(=O)—HN—CH₂—CH₂—O—P(=O)(C₆H₁₃)—O—C₆H₄—NO₂ (NBD group) | XXXI | 0.04[b] | n.d. | 11.1 |
| HN—(CH₂)₅—C(=O)—HN—CH(CH₂—O—P(=O)(C₆H₁₃)—O—C₆H₄—NO₂)(CH₂—O—C₈H₁₇) (NBD group) | XXIV | 0.16[b] | n.d. | 27.8 |
| HN—(CH₂)₁₁—C(=O)—HN—CH(CH₂—O—P(=O)(C₆H₁₃)—O—C₆H₄—NO₂)(CH₂—O—C₁₆H₃₃) (NBD group) | XXV | 0.55[b] | n.d. | 4.4 | n.d. = not detectable
[a] System for TLC: chloroform/methanol/acetone, 10:0.2:0.2 by vol.;
[b] In chloroform/methanol/acetone, 10:0.5:0.5 by vol.

As a second class of lipase inhibitors, phosphonates containing single-chain alkoxy groups instead of glycerolipids were prepared as follows (FIG. 2). Typically, NBD-hexanoic acid succinimide ester was reacted with aminoethanol yielding derivative (XXX). Phosphorylation of the latter compound gave phosphonate (XXXI) with 11.1% yield.

The proton signals in the $^1$H-NMR-spectrum of phosphonate (XXII) were consistent with the indicated molecular structure. Since the phosphorylation procedures for all glycerolipids in this study were identical, only one proton NMR spectrum for the latter compound is presented. UV- and fluorescence spectra of all perylene-labelled organophosphorus compounds showed identical $\lambda_{max}$ which are consistent with their assumed chemical structures.

The perylene-(XXII, XXIII, XXVI, XXVII) and NBD-phosphonates (XXIV, XXV, XXXI) had fluorescence maxima at 448 nm and 533 nm in ethanol, typical for NBD containing derivatives, respectively. The ratio of fluorescent label and phosphorus content of all phosphonates was about 1 to 1.15, additionally confirming the structures of the compounds obtained. Moreover, in ESI mass-spectra of the compounds (XXII, XXVI, XXIII, XXVII, XXXI, XXIV, XXV) only signals corresponding to their molecular structures were observed (Table 2).

TABLE 2

Results of mass-spectrometry analysis of organophosphonates.

| Compound number | Formula | Molecular weight | Ions observed | $m/z_{theor}$ | $m/z_{observed}$ |
|---|---|---|---|---|---|
| XXII | $C_{47}H_{57}N_2O_7P$ | 792.39 | $[C_{47}H_{57}N_2O_7P\cdot Cs]^+$ | 925.30 | 925.4 |
| XXVI | $C_{47}H_{57}N_2O_7P$ | 792.39 | $[C_{47}H_{57}N_2O_7P\cdot Cs]^+$ | 925.30 | 925.3 |
| XXIII | $C_{59}H_{81}N_2O_7P$ | 960.58 | $[C_{59}H_{81}N_2O_7P\cdot Cs]^+$ | 1093.48 | 1093.4 |
| XXVII | $C_{59}H_{81}N_2O_7P$ | 960.58 | $[C_{59}H_{81}N_2O_7P\cdot Cs]^+$ | 1093.48 | 1093.4 |
| XXXI | $C_{26}H_{35}N_6O_9P$ | 606.22 | $[C_{26}H_{35}N_6O_9P\cdot Cs]^+$ | 739.13 | 739.3 |
| XXIV | $C_{35}H_{53}N_6O_{10}P$ | 748.36 | $[C_{35}H_{53}N_6O_{10}P\cdot Cs]^+$ | 881.26 | 881.3 |
| XXV | $C_{49}H_{81}N_6O_{10}P$ | 944.58 | $[C_{49}H_{81}N_6O_{10}P\cdot Cs]^+$ | 1077.48 | 1077.3 |

Mass-spectra were recorded as described in "Materials and Methods".

Interaction of Inhibitors with Lipolytic Enzymes

The novel compounds were tested with respect to their ability to inhibit three selected microbial lipases with different substrate preferences. The lipase from *Rhizopus oryzae* was efficiently inactivated by the perylene- and NBD-inhibitors (FIG. 3a) at 4° C. for 16 hrs in 100 μM Tris-HCl puffer at inhibitor and lipase concentrations of 1.0 mM and 0.1 mM, respectively. It is noteworthy that the long-chain inhibitors (XXIII) and (XXVII) were somewhat more active as compared to the corresponding short-chain compounds (XXII) and (XXVI). The long-chain NBD-dodecanoylamino-sn-1-phosphonate (XXV) was slightly more effective than its short-chain counterpart (XXIV). This is in line with the assumption that lipases prefer long-chain glycerol esters as substrates, and evidently inhibitors as well. The two-chain phosphonate (XXII) was a much more potent inhibitor of the lipase from *Pseudomonas cepacia* than the other inhibitors used (FIG. 3b). In contrast, the *Pseudomonas* species lipase was quantitatively inactivated by all synthesized organophosphonates (FIG. 3c).

Lipases may show very different steric constraints around and within their active site, and as a consequence, very different substrate and inhibitor preferences (Pleiss et al., Chem. Phys. Lipids 93, 67-80 (1998)). The lipases ROL, PCL and PSL, which had been chosen for the inhibition experiments with organophosphonates, are typical examples for this structural diversity among highly homologous enzymes. Accordingly, they show different patterns of reactivity not only towards lipid substrates, but also to structurally related inhibitors as demonstrated herein.

As an alternative to water-soluble lipase monomers used in industry, cross-linked enzyme crystals (CLECs) (Khalaf et al., J. Am. Chem. Soc. 118, 5494-5495 (1996); Lalonde et al., J. Am. Chem. Soc. 117, 6845-6852 (1995); Clair et al., J. Am. Chem. Soc. 114, 7314-7316 (1992)) have been introduced to increase enzyme activity (Zelinski et al., Angew. Chem. 109, 746-748 (1997)) and stability in organic solvents (Persichetti et al., 1995). This makes them useful catalysts which are easy to separate from the reaction mixture and can be repeatedly used after subsequent filtration and washing. The inhibitors according to the invention might also be useful to characterize the functional quality of these systems which is otherwise difficult to determine.

The invention claimed is:

1. A method for inhibiting lipolytic enzymes in a biological sample which comprises combining a biological sample with a compound having general formula I

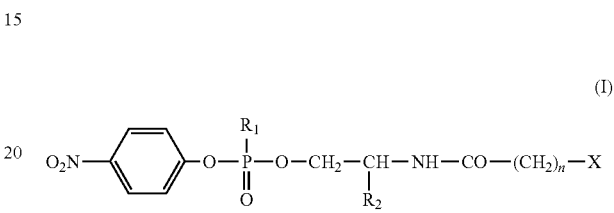

(I)

in which X represents an optically detectable moiety which is a fluorophore, n is an integer with $1 \leq n \leq 20$, $R_1$ is an unbranched or branched alkyl group having 1 to 20 carbon atoms, and $R_2$ is hydrogen or $-CH_2-O-R_3$ group, wherein $R_3$ has the same meaning as $R_1$.

2. A method for analyzing lipolytic enzymes in a biological sample which comprises combining a biological sample with a compound having general formula I

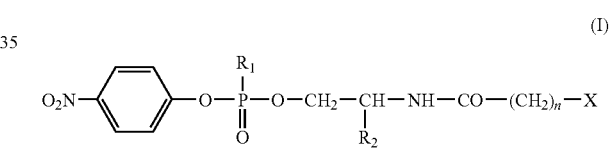

(I)

in which X represents an optically detectable moiety which is a fluorophore, n is an integer with $1 \leq n \leq 20$, $R_1$ is an unbranched or branched alkyl group having 1 to 20 carbon atoms, and $R_2$ is hydrogen or $-CH_2-O-R_3$ group, wherein $R_3$ has the same meaning as $R_1$.

3. The method according to claim 1 or 2, wherein n is an integer with $3 \leq n \leq 11$.

4. The method according to claim 1 or 2, wherein $R_1$ is hexyl and $R_2$ is $-CH_2-O-R_3$ group with $R_3$ being octyl or hexadecyl.

5. The method according to claim 1 or 2, wherein $R_1$ is methyl and $R_2$ is $-CH_2-O-R_3$ group with $R_3$ being octyl or hexadecyl.

6. The method according to claim 1 or 2, wherein $R_1$ is butyl and $R_2$ is $-CH_2-O-R_3$ group with $R_3$ being octyl or hexadecyl.

7. The method according to claim 1 or 2, wherein said fluorophore is selected from the group consisting of perylene, pyrene or nitrobenzoxadiazole.

8. The method according to claim 7 wherein said fluorophore is perylene.

* * * * *